United States Patent [19]

Koizumi et al.

[11] Patent Number: 4,614,427

[45] Date of Patent: Sep. 30, 1986

[54] AUTOMATIC CONTAMINANTS DETECTION APPARATUS

[75] Inventors: Mitsuyoshi Koizumi; Yoshimasa Oshima; Nobuyuki Akiyama, all of Yokohama; Toshiaki Yachi, Kodaira, all of Japan

[73] Assignees: Hitachi, Ltd., Tokyo; Hitachi Electronics Engineering Co., Ltd., Kanagawa, both of Japan

[21] Appl. No.: 611,947

[22] Filed: May 18, 1984

[30] Foreign Application Priority Data

May 20, 1983 [JP] Japan .................................. 58-87686

[51] Int. Cl.⁴ ...................... G01N 21/88; G01N 21/21
[52] U.S. Cl. ........................................ 356/237; 356/73
[58] Field of Search .................. 356/237, 239, 369, 73

[56] References Cited

U.S. PATENT DOCUMENTS 3,790,286  2/1974  Kraus .................................. 356/369
3,850,525  11/1974  Kaye .................................... 356/73
4,342,515  8/1982  Akiba et al. ......................... 356/239

FOREIGN PATENT DOCUMENTS 55-133551  10/1980  Japan .
55-149829  11/1980  Japan .

OTHER PUBLICATIONS

Koizumi et al., "A Polarized Laser Scan Technique for Semiconductor Surface Contaminants Inspection", *International Commision for Optics*, Aug. 1984.

Akiyama et al., "Automatic Inspection of Foreign Particles on Patterned Sample by Means of Polarized Laser", *Transactions of the Society of Instrument and Control Engineers*, pp. 237–242.

*Primary Examiner*—Vincent P. McGraw
*Assistant Examiner*—S. A. Turner
*Attorney, Agent, or Firm*—Antonelli, Terry & Wands

[57] ABSTRACT

An automatic contaminants detection apparatus comprises a polarized laser beam source, a polarized laser beam irradiation optical system having irradiation angle switching means for switching an irradiation angle depending on the presence or absence of a pattern on a sample surface to irradiate the polarized laser beam emitted by the polarized laser beam source to the sample surface with an angle of grazing, a detector for detecting condensed scattered or reflected lights of the laser beam from the sample surface with or without interleave of an analyzer, and analyzer switching means for inserting or removing the analyzer into or from a detection light path of the detector depending on the presence or absence of the pattern on the sample surface. The apparatus can detect contaminants on the patterned or non-patterned sample surface with a high sensitivity.

11 Claims, 12 Drawing Figures

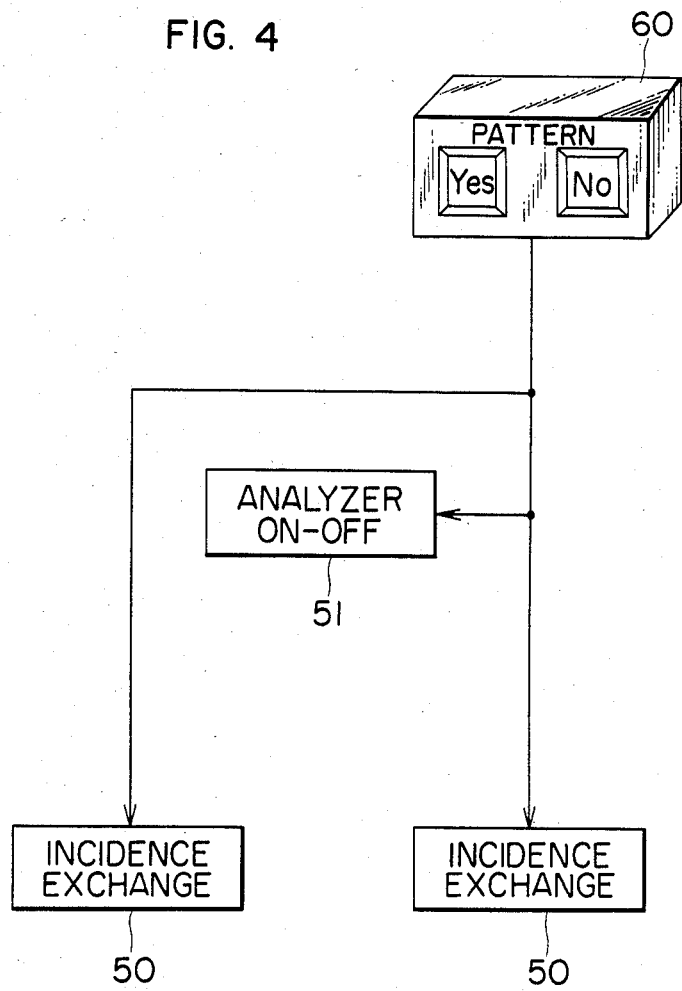

AUTOMATIC CONTAMINANTS DETECTION APPARATUS

BACKGROUND OF THE INVENTION

The present invention relates to an automatic contaminants detection apparatus which detects contaminants or foreign particles on a semiconductor wafer or a photo-mask with a high reliability.

Contaminants have a direct effect on LSI yield. At present, visual inspection of Si wafers for contaminant is an essential part of the semiconductor QC process. However, the conventional QC process requires much time and significantly limits LSI yield. These contaminants are usually dust particles or microscopic silicon particles chipped from the wafer during handling. Therefore, means for detecting these particles to facilitate control of environment conditions and early rejection of the contaminated wafers is needed.

Many automatic detection apparatuses which detect contaminants introduced on a wafer or a photo-mask of a semiconductor device or a magnetic bubble memory during a manufacturing process have been proposed.

In addition to the unpatterned wafer inspection apparatuses, an apparatus for detecting contaminants deposited on a patterned wafer or photo-mask has been proposed. Reference is made to Transactions of the Society of Instrument and Control Engineers Vol. 17, No. 2 (April 1981) pages 237-242, U.S. Pat. No. 4,342,515 and Japanese Patent Application Laid-Open No. 55-149829. Referring to FIG. 1, if a laser beam 4 is simply irradiated to a surface of a wafer or photo-mask 1 at a predetermined grazing angle $\phi$ with respect to the wafer surface, the laser beam 4 is reflected by a pattern 2 and scattered by a contaminant particle 3 as light beams 5 and 6. It is thus difficult to discriminate the scattered beam 6 from the reflected beam 5 and hence the contaminant particle 3 cannot be detected.

Accordingly, a polarized laser beam is used as an irradiating or illuminating beam to detect the contaminants.

As shown in FIG. 2B, when an S-polarized laser beam 10 is irradiated to the pattern 2 on the wafer or photo-mask 1, a reflected light 11 also maintains an S-polarized laser beam component because the surface of the pattern 2 is microscopically smooth. Here, an incident light beam having an electric vector vibrating in a plane parallel to the wafer surface is referred to as "S-polarized" beam. Thus, by arranging an S-polarization cut filter (analyzer) 13 in a reflection (scattered) light path, the reflected light 11 is blocked by the S-polarization cut filter 13 and no light is transmitted upward. On the other hand, as shown in FIG. 2A, when the S-polarized laser beam 10 is irradiated to a contaminant 3, the reflected beam includes an S-polarized laser beam and a P-polarized laser beam 12, because the surface of the contaminants 3 is microscopically rough and the polarization is disturbed and the P-polarized laser beam is generated. Accordingly, by arranging the S-polarization cut filter 13 in the light path, a laser beam 14 transmitted through the S-polarization cut filter 13 includes only the P-polarized laser beam 12. Thus, by detecting the laser beam 12, the contaminant 3 can be detected.

However, the semiconductor manufacturing process includes many steps such as etching, CVD, exposing, resist application and deposition, and the contaminants or deposition of the foreign particles should be detected by the automatic contaminants detection apparatus in each step. It is possible with the above-described automatic contaminants detection apparatus to detect the deposition of the foreign particles on the patterned semiconductor wafer or photo-mask. In this case, a minimum diameter of the contaminants to be detected is 2-3 $\mu$m in view of the detection of the contaminants. On the other hand, in order to improve a yield of IC's, it is necessary to detect contaminants on the surface of the non-patterned smooth semiconductor wafer or photo-mask 1 in a first step to select the non-defect wafer or photo-mask almost free of contaminants, and send the non-defect wafer or photo-mask to the next step. In this case, a minimum size of the contaminants to be detected is 0.3-0.5 $\mu$m. If such fine contaminants are to be detected by the above-mentioned automatic contaminants detection apparatus, an S/N ratio is low and the contaminants cannot be detected at a high sensitivity.

SUMMARY OF THE INVENTION

It is an object of the present invention to provide an automatic contaminants detection apparatus which can stably detect contaminants on a non-patterned wafer as well as those on a patterned wafer with a high sensitivity.

When the contaminants deposited on the non-patterned substrate such as wafer or photo-mask is to be detected by an automatic contaminants detection apparatus adapted to detect the contaminants on a patterned substrate, an analyzer and a small grazing angle (complementary angle of incident angle) $\phi$ which are required for the detection of the contaminants on the patterned substrate are unnecessary or disturbing for the detection of the contaminants on the non-patterned substrate and they lower the detection sensitivity. The present invention can be summarized as follows.

(1) An analyzer (polarization cut filter) in front of a photo-electric device which receives scattered lights from the contaminants is inserted into or removed from a detection light path depending on the presence or absence of the circuit pattern on the surface to be tested.

(2) A grazing angle of a laser beam to the surface to be tested is switchable or exchangeable depending on the presence or absence of the pattern on the surface to be tested.

By adding the above functions (1) and (2), the non-patterned smooth wafer or photo-mask can be tested with the accuracy of the prior art automatic contaminants detection apparatuses without degrading the respective performance. Thus, a value of the contaminants detection apparatus is increased.

BRIEF DESCRIPTION OF THE DRAWINGS

FIG. 4 shows an embodiment for cooperating a switching mechanism shown in FIG. 3, FIGS. 5A and 5B illustrate a working principle of the apparatus of FIG. 3.

DESCRIPTION OF THE PREFERRED EMBODIMENTS

Before the description of the preferred embodiments, operational principles of the contaminants inspection apparatus will be briefly described.

Incident light is focused in a spot on a wafer at an oblique angle incidence. An objective lens for collecting detection lights is disposed above the light spot so that lights specularly reflected by the wafer surface is not incident on the objective. Thus, only those lights which are scattered or reflected by contaminants or patterns on the wafer are incident on the objective. Lights from pattern lines which make an angle above a threshold angle are not collected by the objective lens. Some contaminants have anisotropic shapes. Then, two or more light projection systems may be provided for enhancing the reliability, stability and uniformity.

The angle of oblique incidence has different technical effects on the detection of objects of any kind and the discrimination of pattern and contaminants. Higher intensity is desirable for detection of an object of any kind. For this purpose the light spot on the wafer is better focused in small dimensions. The supplementary angle of incident angle will be referred to as grazing angle in this specification. Then, the grazing angle is higher the better for obtaining small spot dimensions and hence a higher intensity. For discriminating contaminants and patterns, the grazing angle is lower the better as will be described in more detail later. For satisfying these contradictory requirements in one inspection apparatus, the present invention proposes to provide switchable incident optical systems.

Figure 1:
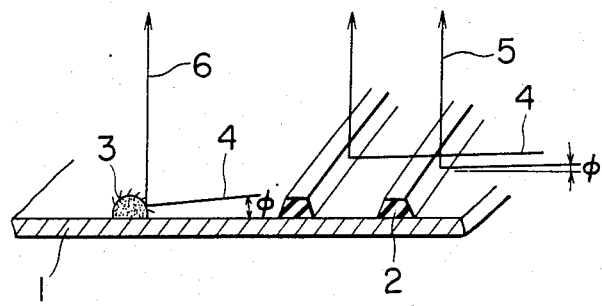
FIG. 1 illustrates a drawback caused when a polarized laser beam is not used.
Figure 2A:
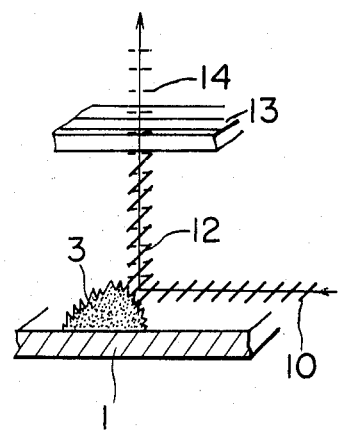
FIGS. 2A and 2B illustrate a principle of contaminants detection by a polarized laser beam.
Figure 2B:
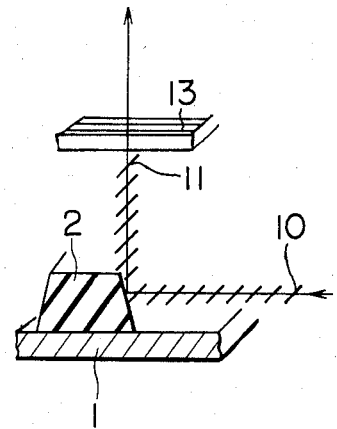
Figure 3:
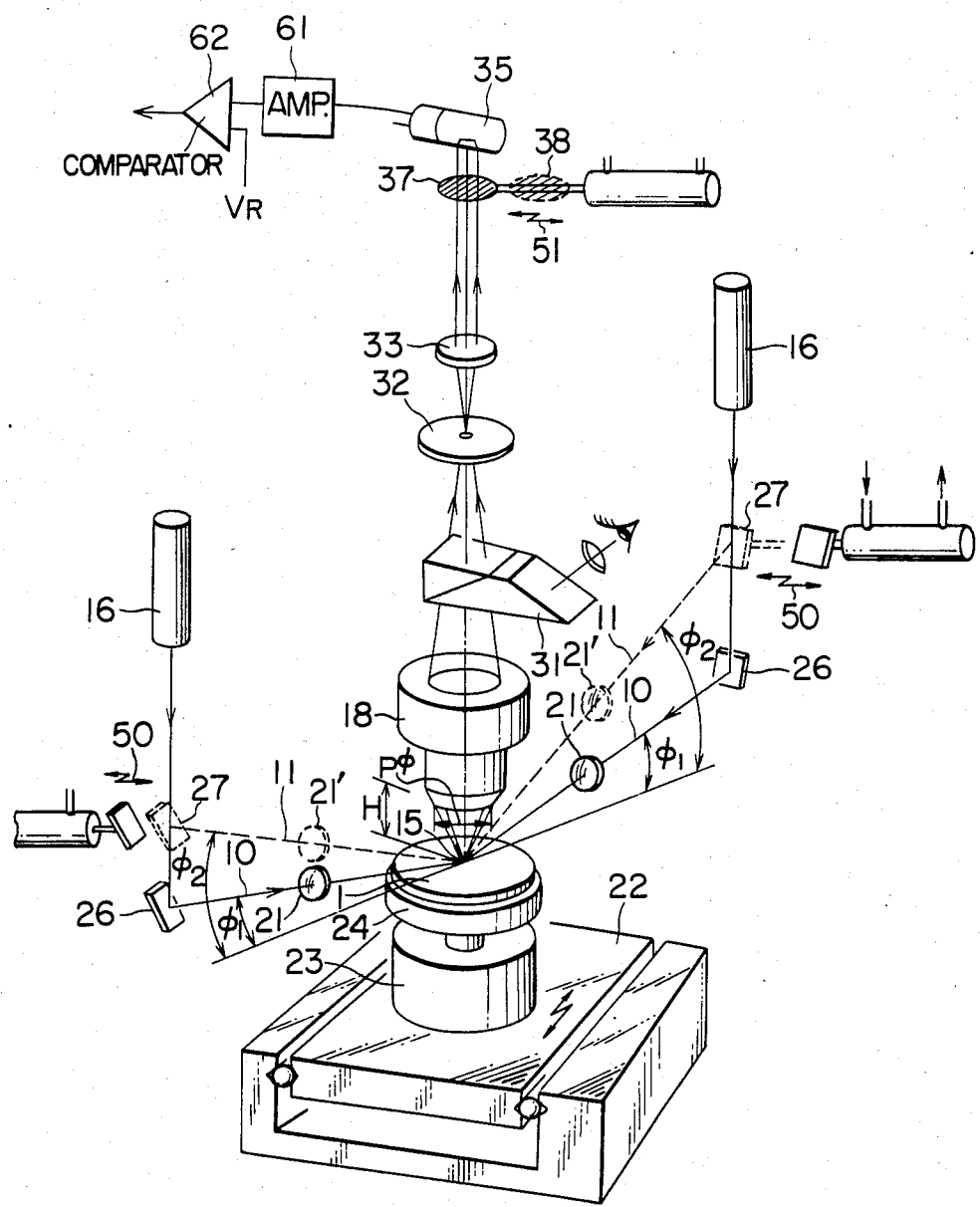
FIG. 3 shows one embodiment of a contaminants detection apparatus of the present invention.

FIG. 3 shows an embodiment of the present invention. Reference is made generally to Japanese Patent Application Laid-Open No. 55-133551, U.S. Pat. No. 4,342,515 and the above mentioned documents. A wafer 1 which is a sample under test is mounted on a sample stage 24 connected to a rotary drive 23 on a feed stage 22 which enable a constant speed helical scan of a point 15 under test. An S-polarized laser beam (having a light flux diameter D of approximately 1 mm) 10 (11) emitted from each He-Ne (wavelength 6328Å) or semiconductor laser 16 is deflected by a mirror 26 or 27, focused by a lens 21 or 21' and irradiated to the surface under test. A scattered or reflection light of the S-polarized laser beam 10 (11) randomly reflected by the contaminants or patterns on the surface 1 is focused by an object lens 18, transmitted through a pinhole 32, a field lens 33 and an analyzer (S-polarization cut filter) 37, and detected by a photo-electric device 35 such as a photo-multiplier tube. The objective lens 18 may be an extra long working distance lens. In this case, a leading diameter P is approximately 23 mm and a distance H from a leading end to the wafer 1 is approximately 12 mm.

Figure 5A:
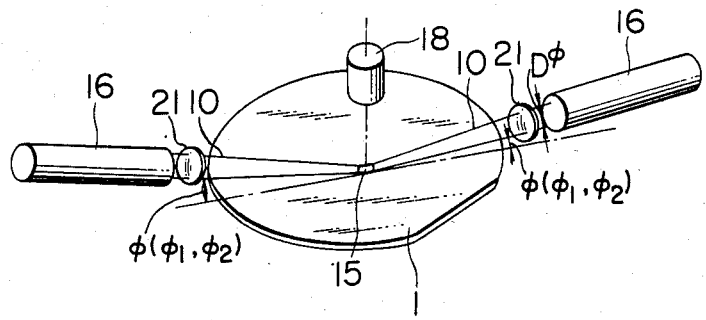
Figure 5B:
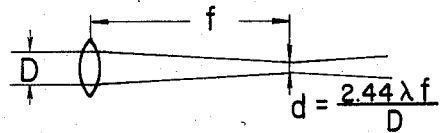

The projection of a light spot on a wafer is illustrated in FIGS. 5A and 5B. In FIG. 5A, each of laser sources 16 emits a parallel laser light flux (diameter $D^\phi$) which is focused by a lens 21 into a spot 15. When there exists a contaminant particle or a pattern at the spot 15, the laser beam flux or fluxes will generate scattered or reflected lights which can be collected by the objective lens 18.

FIG. 5B shows the focus of a laser beam by a lens of a focal length f. A laser light flux of a diameter D and a wavelength $\lambda$ is focused to a flux of a diameter $d = 2.44 \lambda f/D$ on the focal plane at the focal distance f of the lens. When the wafer is normal to the flux, the light spot formed by the light flux will be minimum. When the wafer is inclined to low grazing angles, the light spot will be elongated.

Figure 8A:
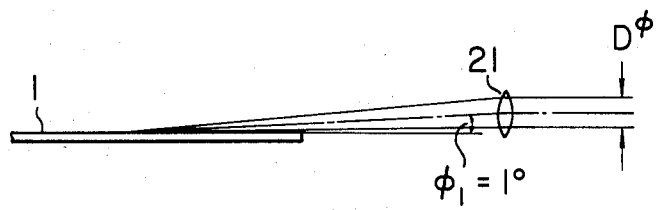
FIG. 8A illustrates a laser beam focused by a cylindrical lens and irradiated to the wafer at an angle $\phi_1$.
Figure 8B:
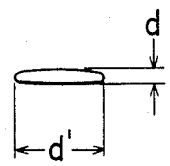
FIG. 8B shows a spot on the wafer for the laser beam shown in FIG. 8A.

When the wafer 1 under test is a patterned wafer, a grazing angle $\phi_1$ of the laser beam to the surface under test is made small as will be explained later. The laser beam 10 is deflected by the mirror 26, focused to d = 230 $\mu$m by the lens 21 having a focal distance f of approximately 150 mm and projected on the wafer as shown in FIG. 8A. The wafer surface at the point 15 under test is irradiated with an elliptic spot with a long diameter d' = 13.2 mm as shown in FIG. 8B. The scattered and/or reflection light beams from the surface under test and collected by the objective lens 18 are transmitted through the analyzer (S-polarization cut filter) 37 and sensed by the photo-electric conversion device 35 to detect contaminants on the patterned wafer. The light flux diameter focused by the lens 21 is equal to $d = 2.44 \lambda f/D$ where $\mu$ is 0.63 $\mu$m (for the He-Ne laser).

Figure 6:
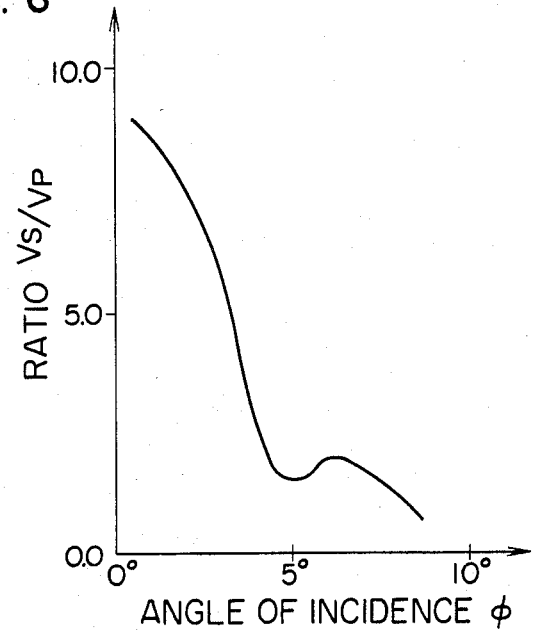
FIG. 6 shows a relation between a grazing angle $\phi$ and a ratio Vs/Vp of a contaminant detection output Vs to a pattern output Vp.

Since the surface of the patterned wafer is microscopically smooth, the reflection light from the circuit pattern maintains the S-polarized laser beam component which is blocked by the analyzer (S-polarization cut filter) 37. On the other hand, the scattered light from the contaminants includes the S-polarized laser beam and the P-polarized laser beam. The latter transmits through the analyzer (S-polarization cut filter) 37 and it is detected by the photo-electric conversion device 35 so that the contaminants on the circuit pattern is detected. When the wafer 1 under test carries the circuit pattern, the grazing angle $\phi_1$ is preferably 1°-2° taking a design matter into consideration. A ratio Vs/Vp, which is a kind of device figure of merit, varies with the grazing angle $\phi$ as shown in FIG. 6 where Vs and Vp are outputs of the photo-electric conversion device when a contaminant is present at the point 15 under test and when a circuit pattern exists on the wafer 1 under test respectively. At low grazing angles, the merit ratio Vs/Vp is the higher as the grazing angle is the lower. A high Vs/Vp ratio means that signal level varies greatly depending on whether a pattern or a contaminant particle is irradiated.

Accordingly, the discrimination of Vs and Vp is easier and the contaminants detection sensitivity is higher when the grazing angle $\phi$ is small than when it is large. Accordingly, the grazing angle is set to a small angle, preferably 1°-2° taking the design matter into consideration. FIGS. 8A and 8B show laser beam irradiation and a spot shape on the wafer under this condition.

Figure 7A:
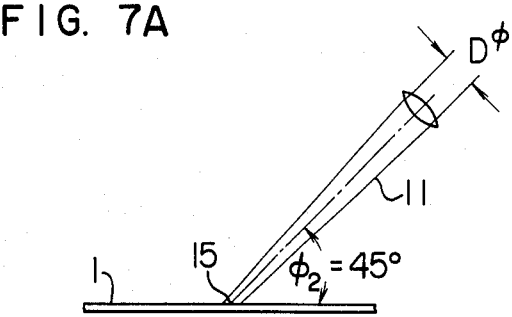
FIGS. 7A and 7B illustrate a laser beam irradiated to a wafer at an angle $\phi_2$.
Figure 7B:
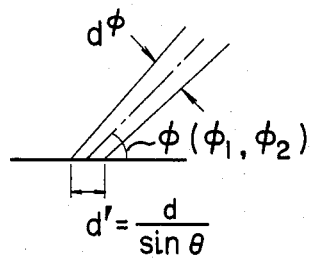

When the wafer 1 under test has no circuit pattern and is a smooth wafer, the grazing angle $\phi_2$ of the S-polarized irradiation laser beam measured with respect to the surface under test is preferably made large, that is, the laser beam 11 instead of the beam 10 should be used. To this end, a switching mechanism such as an air cylinder is provided to insert the mirror 27 into the optical path so that the laser beam having the light flux diameter $D_\phi$ is reflected by the mirror 27 and the grazing angle is switched to approximately 45° to increase irradiation light intensity per unit area so that an intense light is irradiated to the point 15 under test. FIGS. 7A and 7B show the laser beam irradiation under this condition. When the object lens 18 described above is used and the grazing angle $\phi_2$ is designed over 45°, it becomes difficult from the structural limitations to irradiate the beam onto the semiconductor wafer and the specularly reflected light may impinge the object lens 18.

Referring to FIG. 7B, the long diameter d' of the elliptic spot, $d'=d/\sin\phi$, is decreased with the increase of the grazing angle $\phi$. The light intensity at the spot is increased due to the reduction of the spot area. Usually, the contaminant particles to be detected are far smaller than the light spot dimensions. Thus the high intensity in the spot area will produce high intensity of scattered light and a high S/N ratio.

The analyzer (S-polarization cut filter) 37 is driven by an air cylinder mechanism to be located at a position 38 away from the detection light path. Accordingly, when the wafer under test is the smooth wafer, the irradiation light intensity per unit area is increased, and all of the scattered lights from the contaminants (both S-polarization and P-polarization) are detected by the photo-electric conversion device 35 so that the output level and the S/N ratio of the photo-electric conversion device are increased. Thus, the contaminants can be detected with a high sensitivity and an influence by an external light is reduced.

By the combination of the linear movement (radial direction) of the feed stage 22 and the rotating movement (azimuthal direction) of the sample stage 24, the point 15 under test is helically scanned on the wafer 1 at a constant circumferential speed. The signal detected by the photo-electric conversion device 35 is amplified by an amplifier 61, an output of which is compared with a predetermined threshold $V_R$ by a comparator 62, which produces a signal when the contaminants exist. The tolerance of the slice level depends on the Vs/Vp ratio as described before.

The analyzer switching mechanism 51 and the irradiation angle switching mechanism may be of simple structure having a manual insertion/removal function, but in order to prevent misoperation by an operator, it is desirable to use air-cylinder controlled by electric signal, a motor-driven automatic switching mechanism, etc. as shown in FIG. 4, having a cooperation function for cooperating the switching mechanisms 50 and 51 by a switch 60 which is switched depending on the presence or absence of the pattern. The cooperation mechanism may be implemented by mechanical means. The implementation by electrical means is simpler.

The larger the angle $\phi_2$ is, the larger is the light intensity per unit area and the higher is the detection sensitivity for the contaminants on the non-patterned smooth wafer. This is shown in Table 1.

While the detection of the contaminants on the semiconductor wafer has been specifically described above, the deposition of the contaminants on the photo-mask can be similarly detected for the patterned and non-patterned photo-masks.

As described hereinabove, according to the present embodiment, the S/N ratio of the detection signal is about 206 times improved over the prior art apparatus for the detection of the contaminants on the non-patterned smooth wafer or photo-mask (because the light intensity or the signal level is improved by a factor of approximately 5 by the removal of the analyzer and approximately 40 by the change of the irradiation angle ($\phi_1=1°\rightarrow\phi_2=45°$)). Thus, both the patterned and non-patterned smooth wafers or photo-masks can be tested by the same automatic contaminants detection apparatus with a high detectivity to the fine contaminants on the smooth wafer or photo-mask

We claim:

1. An automatic contaminants detection apparatus comprising:
   a polarized laser beam source;
   a polarized laser beam irradiation optical system for irradiating the polarized laser beam emitted from said polarized laser beam source to a sample surface with one of first and second angles of grazing, said polarized laser beam irradiation optical system including a grazing angle switching means for switching between the first and second angles of grazing depending on the presence or absence of a pattern on the sample surface, the second angle of grazing being larger than the first angle of grazing;
   a detector for condensing scattered or reflected lights of the laser beam from the sample surface and detecting the condensed light with or without interleave of an analyzer; and
   analyzer switching means for inserting or removing said analyzer into or from a detection light path of said detector depending on the presence or absence of a pattern on the sample surface.

2. An automatic contaminants detection apparatus according to claim 1 wherein said analyzer switching means and said grazing angle switching means are electrically or mechanically cooperated.

3. An automatic contaminants detection apparatus according to claim 1, wherein the first angle of grazing is in the range of 1°–2° the second angle of grazing is in the range of 30°–45°.

4. An automatic contaminants detection apparatus according to claim 1, wherein said polarized laser beam irradiation optical system irradiates the polarized laser beam to the sample surface from a first direction, and further comprising another polarized laser beam irradiation optical system for irradiating the laser beam emit-

TABLE 1

| $\phi$ | 1° ($\phi_1$) | 10° | 20° | 30° | 40° | 45° |
|---|---|---|---|---|---|---|
| d | 230 μm | 230 μm | 230 μm | 230 μm | 230 μm | 230 μm |
| d' | 13.2 mm | 1.32 mm | 0.67 mm | 0.46 mm | 0.36 mm | 0.32 mm |
| Signal level | | | | | | |
| with polarizer | 1 | 10 | 19.7 | 28.6 | 36.7 | 41.3 |
| without polarizer (×5) | 5 | 50 | 98 | 143 | 184 | 206 |

The signal level indicates the intensity of the signal light which increases with the increase of the grazing angle $\phi$ and removal of the analyzer (approximately 5 times).

Thus, the angle $\phi_2$ is preferably selected to 30°–45°.

ted from said polarized laser beam source to the sample surface with one of the first and second angles of grazing from a second direction.

5. An automatic contaminants detection apparatus according to claim 1, wherein said grazing angle switching means includes a movable mirror inserted into the optical path of the polarized laser beam emitted from said polarized laser beam source.

6. An automatic contaminants detection apparatus for detecting contaminants on a wafer or a mask, comprising:
a polarized laser beam source;
a polarized laser beam irradiation optical system for irradiating the polarized laser beam emitted from the polarized laser beam source to a surface of the wafer or mask with one of first and second angles of grazing, the polarized laser beam irradiation optical system including grazing angle switching means for switching between the first and second angles of grazing in dependence upon the presence or absence of a circuit pattern on the surface of the wafer or mask, the second angle of grazing being larger than the first angle of grazing; and
a detector for condensing scattered or reflected lights of the laser beam from the surface of the wafer or mask by an objective lens and detecting the condensed light through a pinhole, the detector including detection means for receiving the condensed light from the pinhole whether or not the condensed light passes through an analyzer, the detector including analyzer switching means for inserting or removing the analyzer into or from a detection light path in cooperation with the grazing angle switching means in dependence upon the presence or absence of the circuit pattern on the surface of the wafer or mask.

7. An automatic contaminants detection apparatus according to claim 6, wherein the first angle of grazing is in the range of 1°–2° and the second angle of grazing is in the range of 35?–45°.

8. An automatic contaminants detection apparatus according to claim 6, wherein the grazing angle switching means includes a movable mirror inserted into the optical path of the polarized laser beam emitted from the polarized laser beam source.

9. An automatic contaminants detection apparatus according to claim 6, wherein the polarized laser beam irradiation optical system includes a condenser lens for focusing the laser beam emitted from the polarized laser beam source onto the surface of the wafer or mask.

10. A method for detecting contaminants on a surface of a wafer or mask comprising the steps of:
irradiating a polarized laser beam emitted from a polarized laser beam source to a surface of the wafer or mask with one of first and second angles of grazing by a polarized laser beam irradiation optical system;
switching the angle of grazing from the first angle of grazing to the second angle of grazing which is larger than the first angle of grazing by a grazing angle switching means in dependence upon the presence or absence of a circuit pattern on the surface of the wafer or mask;
condensing scattered or reflected light of the laser beam from the surface of the wafer or mask by an objective lens; and
detecting the condensed light by a detector through a pinhole whether or not the condensed light passes through an analyzer inserted or removed into or from a detection light path by an analyzer switching means cooperating with the grazing angle switching means to insert the analyzer or remove the analyzer in dependence upon the presence or absence of the circuit pattern of the surface of the wafer or mask.

11. A method for detecting contaminants according to claim 10, wherein the first grazing angle is in the range of 1°–2° and the second grazing angle is in the range of 30°–45°.

* * * * *